(12) United States Patent
Rotem et al.

(10) Patent No.: US 10,112,005 B2
(45) Date of Patent: Oct. 30, 2018

(54) SIZE-EFFICIENT DRUG-DELIVERY DEVICE

(75) Inventors: Nir Rotem, Gedera (IL); Keren Fradkin, Tel Aviv (IL); Jonathan Goldstein, Jerusalem (IL)

(73) Assignee: STEADYMED, LTD., Tel Aviv (IL)

( * ) Notice: Subject to any disclaimer, the term of this patent is extended or adjusted under 35 U.S.C. 154(b) by 0 days.

(21) Appl. No.: 13/825,806

(22) PCT Filed: Sep. 26, 2011

(86) PCT No.: PCT/IL2011/000757
§ 371 (c)(1),
(2), (4) Date: Oct. 11, 2013

(87) PCT Pub. No.: WO2012/042517
PCT Pub. Date: Apr. 5, 2012

(65) Prior Publication Data
US 2014/0148761 A1    May 29, 2014

Related U.S. Application Data

(60) Provisional application No. 61/386,567, filed on Sep. 27, 2010.

(51) Int. Cl.
*A61M 5/145* (2006.01)
*A61M 5/142* (2006.01)

(52) U.S. Cl.
CPC .... *A61M 5/14593* (2013.01); *A61M 5/14244* (2013.01)

(58) Field of Classification Search
CPC ...... A61M 3/0237; A61M 2005/14204; A61M 2005/2013; A61M 5/1483; A61M 5/14276; A61M 5/2053; A61M 5/14526; A61M 5/14244; A61M 5/14248; A61M 2005/14506; A61M 2005/14513;
(Continued)

(56) References Cited

U.S. PATENT DOCUMENTS 4,842,598 A    6/1989    Tran
4,843,598 A    6/1989    Medlin
(Continued)

FOREIGN PATENT DOCUMENTS

CA    2812877 A1    4/2012
DE    3621846 A1    1/1988
(Continued)

OTHER PUBLICATIONS

European Search report dated Mar. 4, 2016 in European Patent Application 11782228.8, all pages.
(Continued)

*Primary Examiner* — Bhisma Mehta
*Assistant Examiner* — William Frehe
(74) *Attorney, Agent, or Firm* — Kilpatrick Townsend & Stockton LLP

(57) ABSTRACT

A drug-delivery device comprising a drug-reservoir assembly, displacement-generating actuator, and drug administration unit is described, wherein the drug-reservoir assembly comprises at least one flexible wall and a constraining ring, such that the displacement generated by the actuator collapses a flexible wall of the assembly expelling the drug contents of the drug-reservoir towards said drug administration means.

26 Claims, 6 Drawing Sheets

(58) Field of Classification Search
CPC ...... A61M 5/1452; A61M 2005/14533; A61M 5/1454; A61M 5/14546; A61M 2005/14553; A61M 5/1456; A61M 5/14566; A61M 2005/14573
USPC .................. 604/890.1, 891.1, 131, 140–146
See application file for complete search history.

(56) References Cited

U.S. PATENT DOCUMENTS

| | | | |
|---|---|---|---|
| 4,886,514 A | 12/1989 | Maget | |
| 5,062,834 A | 11/1991 | Gross et al. | |
| 5,102,389 A * | 4/1992 | Hauser | A61M 39/0208 |
| | | | 128/DIG. 12 |
| 5,108,852 A | 4/1992 | Tomantschger et al. | |
| 5,109,850 A | 5/1992 | Blanco et al. | |
| 5,134,046 A | 7/1992 | Chow et al. | |
| 5,318,557 A | 6/1994 | Gross | |
| 5,354,264 A | 10/1994 | Bae et al. | |
| 5,436,372 A | 7/1995 | Yoshida et al. | |
| 5,438,249 A | 8/1995 | Chang et al. | |
| 5,505,706 A | 4/1996 | Maus et al. | |
| 5,527,288 A | 6/1996 | Gross et al. | |
| 5,563,004 A | 10/1996 | Buzzelli et al. | |
| 5,643,207 A | 7/1997 | Rise | |
| 5,677,083 A | 10/1997 | Tomiyama | |
| 5,814,020 A | 9/1998 | Gross | |
| 5,827,233 A * | 10/1998 | Futagawa | A61M 5/2425 |
| | | | 604/218 |
| 5,848,991 A | 12/1998 | Gross et al. | |
| 5,938,640 A * | 8/1999 | Maget | A61M 5/1413 |
| | | | 604/131 |
| 5,980,741 A | 11/1999 | Schnell et al. | |
| 6,150,053 A | 11/2000 | Murata et al. | |
| 6,186,982 B1 | 2/2001 | Gross et al. | |
| 6,296,967 B1 | 10/2001 | Jacobs et al. | |
| 6,312,409 B1 * | 11/2001 | Gross | A61M 5/14593 |
| | | | 604/131 |
| 6,322,532 B1 | 11/2001 | D'Sa et al. | |
| 6,358,239 B1 * | 3/2002 | Rake | A61M 5/148 |
| | | | 128/DIG. 12 |
| 6,377,848 B1 | 4/2002 | Garde et al. | |
| 6,400,489 B1 | 6/2002 | Suzuki et al. | |
| 6,465,125 B1 | 10/2002 | Takami et al. | |
| 6,506,520 B1 | 1/2003 | Inoue et al. | |
| 6,534,218 B1 | 3/2003 | Okada et al. | |
| 6,537,249 B2 * | 3/2003 | Kriesell | A61M 5/14248 |
| | | | 128/DIG. 12 |
| 6,537,250 B1 | 3/2003 | Kriesel | |
| 6,577,039 B2 | 6/2003 | Ishida et al. | |
| 6,589,229 B1 | 7/2003 | Connelly et al. | |
| 6,733,485 B1 | 5/2004 | Whitehurst et al. | |
| 6,982,514 B1 | 1/2006 | Lu et al. | |
| 7,108,686 B2 * | 9/2006 | Burke | A61M 5/14276 |
| | | | 604/131 |
| 7,242,134 B2 | 7/2007 | Wallace et al. | |
| 7,364,568 B2 | 4/2008 | Angel et al. | |
| 7,541,715 B2 | 6/2009 | Chiang et al. | |
| 8,834,454 B2 | 9/2014 | Genosar et al. | |
| 9,011,376 B2 | 4/2015 | Goldstein | |
| 2002/0107480 A1 | 8/2002 | Kriesel et al. | |
| 2002/0156461 A1 | 10/2002 | Joshi | |
| 2002/0169439 A1 | 11/2002 | Flaherty | |
| 2003/0014014 A1 | 1/2003 | Nitzan | |
| 2003/0205582 A1 | 11/2003 | Joshi et al. | |
| 2004/0059282 A1 | 3/2004 | Flock et al. | |
| 2004/0068224 A1 | 4/2004 | Couvillon, Jr. et al. | |
| 2004/0115068 A1 | 6/2004 | Hansen et al. | |
| 2004/0115523 A1 | 6/2004 | Hommura et al. | |
| 2004/0115530 A1 | 6/2004 | Maeda et al. | |
| 2004/0116847 A1 * | 6/2004 | Wall | A61K 9/0019 |
| | | | 604/93.01 |
| 2004/0138612 A1 | 7/2004 | Shermer et al. | |
| 2005/0096587 A1 | 5/2005 | Santini et al. | |
| 2006/0052768 A1 | 3/2006 | Joshi et al. | |
| 2006/0069344 A1 | 3/2006 | Southam et al. | |
| 2006/0102455 A1 | 5/2006 | Chiang et al. | |
| 2006/0106346 A1 | 5/2006 | Sullivan et al. | |
| 2006/0200073 A1 | 9/2006 | Radmer et al. | |
| 2008/0188779 A1 | 8/2008 | Vallero | |
| 2008/0215029 A1 * | 9/2008 | Rake | A61M 5/148 |
| | | | 604/408 |
| 2008/0281270 A1 | 11/2008 | Cross et al. | |
| 2009/0069746 A1 | 3/2009 | Miller et al. | |
| 2009/0093772 A1 | 4/2009 | Genosar et al. | |
| 2010/0022992 A1 | 1/2010 | Genosar et al. | |
| 2010/0056874 A1 * | 3/2010 | Dijksman | A61B 5/073 |
| | | | 600/300 |
| 2010/0130931 A1 * | 5/2010 | Yodfat | A61M 5/14248 |
| | | | 604/151 |
| 2010/0152658 A1 | 6/2010 | Hanson et al. | |
| 2010/0266638 A1 | 10/2010 | Turkel et al. | |
| 2010/0274221 A1 | 10/2010 | Sigg et al. | |
| 2011/0098652 A1 | 4/2011 | Hasted et al. | |
| 2011/0160655 A1 | 6/2011 | Hanson et al. | |
| 2011/0306929 A1 | 12/2011 | Levesque et al. | |
| 2012/0041338 A1 | 2/2012 | Chickering, III et al. | |
| 2012/0042517 A1 | 2/2012 | Tronnes et al. | |
| 2012/0238849 A1 | 9/2012 | Holtzclaw et al. | |
| 2014/0163339 A1 | 6/2014 | Goldstein et al. | |
| 2014/0171867 A1 | 6/2014 | Walsh et al. | |
| 2015/0017493 A1 | 1/2015 | Genosar et al. | |
| 2015/0038907 A1 | 2/2015 | Rotem | |
| 2015/0045718 A1 | 2/2015 | Shlomo et al. | |
| 2016/0361491 A1 | 12/2016 | Shaked et al. | |
| 2018/0035935 A1 | 2/2018 | Goldstein et al. | |

FOREIGN PATENT DOCUMENTS

| | | |
|---|---|---|
| DE | 19809483 A1 | 9/1999 |
| EP | 0676214 A1 | 10/1995 |
| EP | 1912690 A1 | 4/2008 |
| EP | 2621558 A1 | 8/2013 |
| EP | 2825225 A1 | 1/2015 |
| EP | 2827923 A1 | 1/2015 |
| GB | 2221394 A | 2/1990 |
| IL | 169807 | 2/2006 |
| JP | 02-131376 A | 5/1990 |
| JP | 04-127885 A | 4/1992 |
| WO | 97/010012 A1 | 3/1997 |
| WO | 2001/021234 A1 | 3/2001 |
| WO | 01/51108 A1 | 7/2001 |
| WO | WO0151108 A1 | 7/2001 |
| WO | 2002/069935 A1 | 9/2002 |
| WO | 2004/067066 A1 | 2/2003 |
| WO | 2004/006982 A2 | 1/2004 |
| WO | 2005/124918 A2 | 12/2005 |
| WO | 2007/010522 A1 | 1/2007 |
| WO | 2007/129317 A1 | 11/2007 |
| WO | 2008/062335 A1 | 5/2008 |
| WO | WO2008062335 A1 | 5/2008 |
| WO | 2008/122983 A1 | 10/2008 |
| WO | 2011/075100 A1 | 6/2011 |
| WO | 2012/042517 A1 | 4/2012 |
| WO | 2013/136237 A1 | 9/2013 |
| WO | 2013/140395 A1 | 9/2013 |

OTHER PUBLICATIONS

Lee et al., "Battery Dimensional Changes Occuring During Charge/Discharge Cycles—Thin Rectangular Lithium Ion and Polymer Cells," Journal of Power Sources, 119-121: 833-837 (2003).
European Search Report dated Apr. 13, 2016 for European Patent Application 15171662.8, all pages.
International Search Report and Written Opinion for PCT/IL2007/000548 dated Sep. 18, 2007, all pages.
International Search Report and Written Opinion for PCT/IL2006/000769 dated Oct. 30, 2006, all pages.
International Preliminary Report on Patentability for PCT/IL2006/000769 dated Jan. 22, 2008, all pages.
International Search Report and Written Opinion for PCT/IL2013/050223 dated Jun. 24, 2013, all pages.

(56) References Cited

OTHER PUBLICATIONS

International Preliminary Report on Patentability for PCT/IL2013/050223 dated Sep. 16, 2014, all pages.
International Search Report and Written Opinion for PCT/IL2013/050240 dated Jul. 2, 2013, all pages.
International Preliminary Report on Patentability for PCT/IL2013/050240 dated Sep. 23, 2014, all pages.
International Preliminary Report on Patentability for PCT/IL2007/000548 dated Nov. 11, 2008, all pages.
International Search Report and Written Opinion for PCT/IL2011/000757 dated Jan. 11, 2012, all pages.
International Preliminary Report on Patentability for PCT/IL2011/000757 dated Apr. 2, 2013, all pages.
Notice of opposition to a European patent for Patent No. EP 2015806 dated Jun. 1, 2010, 16 pages.
Office Action for EP 11782228 dated Oct. 13, 2017, all pages.

\* cited by examiner

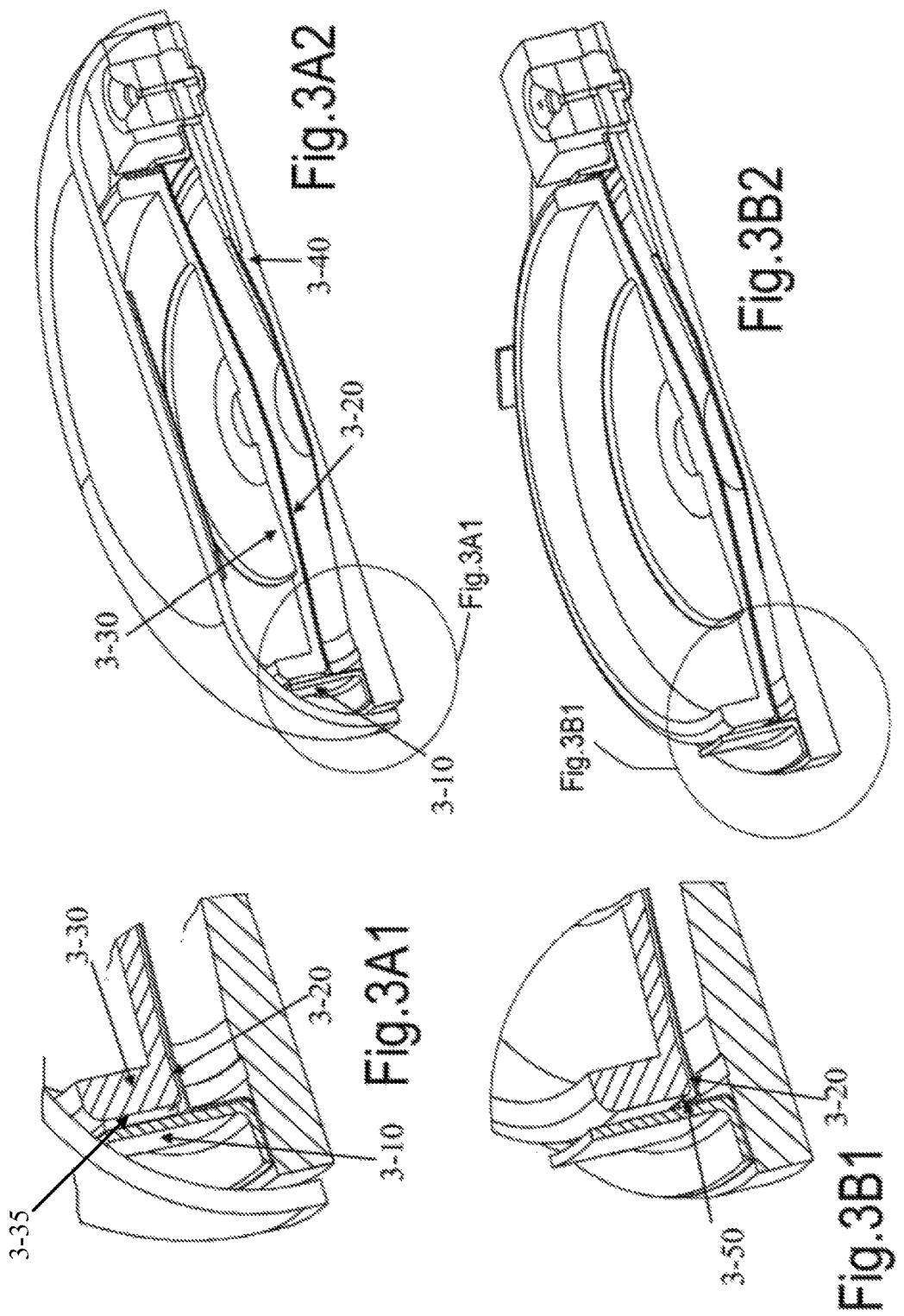

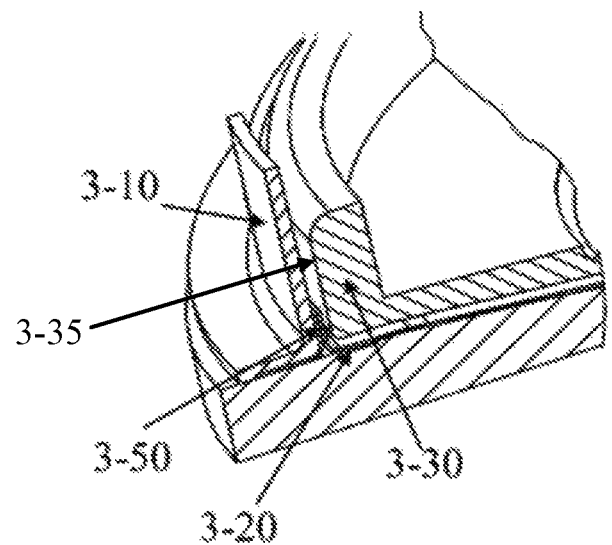
Fig. 3C1
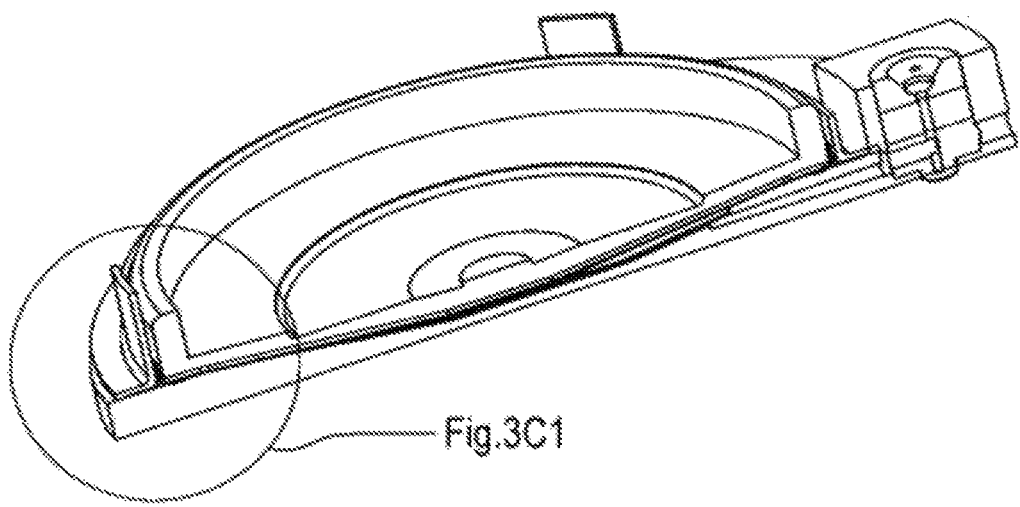
Fig. 3C2

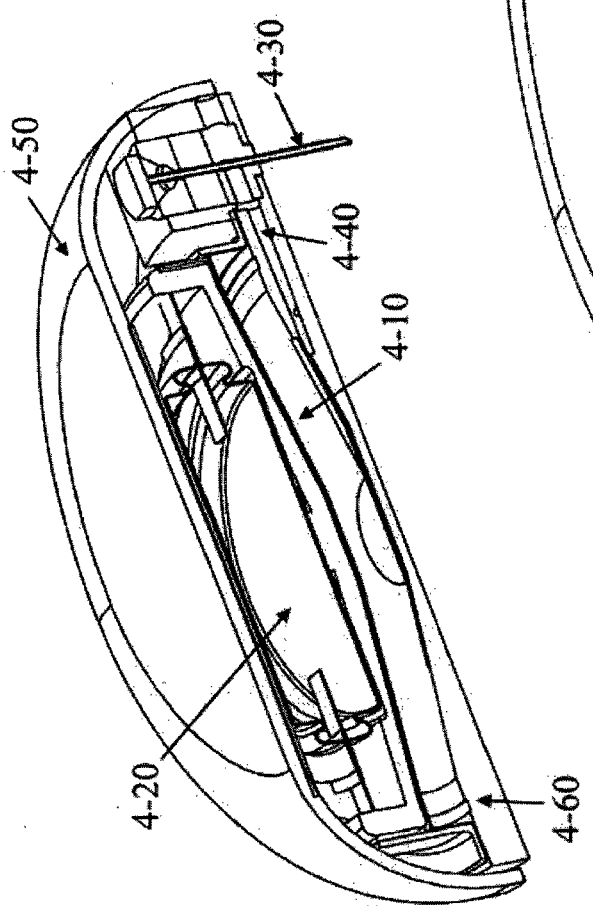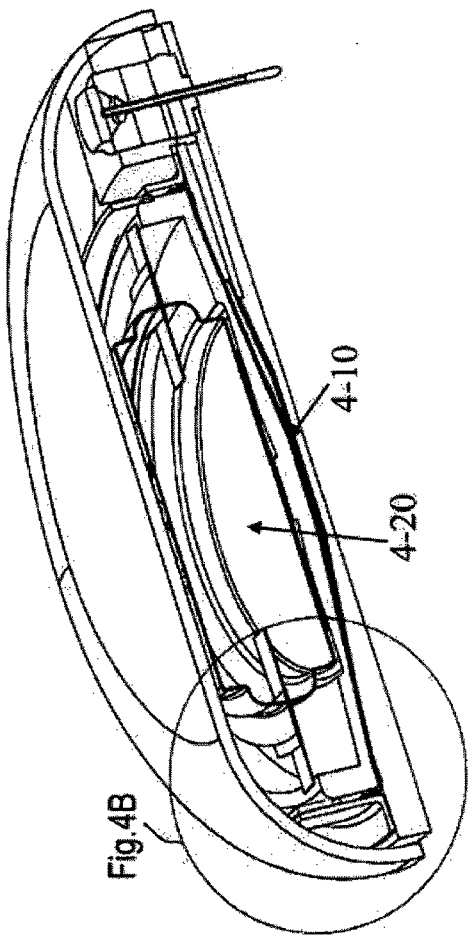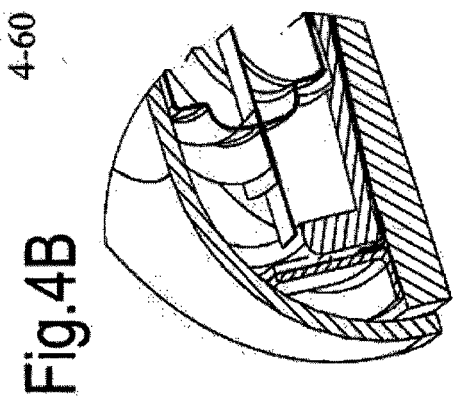

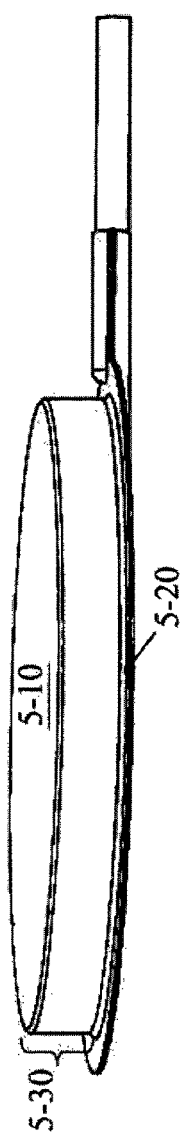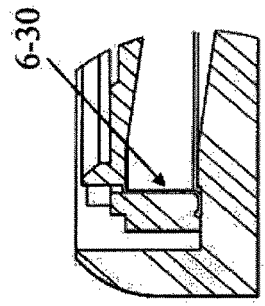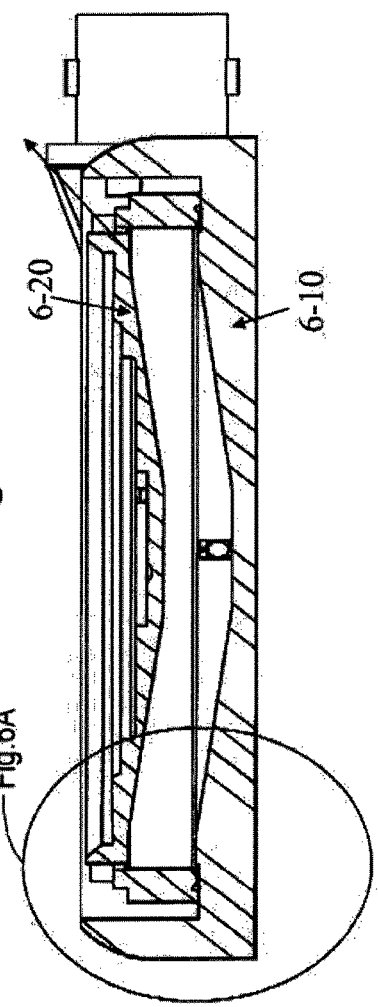

SIZE-EFFICIENT DRUG-DELIVERY DEVICE

FIELD OF THE INVENTION

The present invention provides a patch-pump drug-delivery device providing size-efficient storage and delivery of drugs, and methods of use of the same.

BACKGROUND

The long-term storage of liquid parenteral drugs in pre-filled syringes provides simplicity and convenience for patients and clinicians. The use of such syringes enables skipping the preparatory stage of extracting a drug from a liquid vial (or reconstituting from powder) and then filling into a syringe for injection. An even easier modality of delivering drugs is to use a patch-pump or patch-injector rather than a syringe. The use of such devices reduces "needle shock" and can also enable slow-infusion of drugs in place of rapid injection and facilitate delivery of large-doses of drugs, having a range of viscosities.

The long-term storage of drugs in syringes or other liquid containers requires that those containers be made from a very limited variety of materials, all of which have to be shown to cause minimal damage to the drug contained within even during direct and prolonged contact with the drug. Historically, this material has always been glass, but in more recent years glass syringes have been shown to have some problems and incompatibilities with biological. In particular, numerous drugs—especially biologics—can be adversely affected by the release of soluble alkali from the glass containers. Moreover, there is a known problem of Bovine serum albumin (also known as BSA protein) absorption on the container surface. Additionally, the silicone which is used as a lubricant in a syringe and the tungsten residue from the pin that is used to form the nozzle of the syringe into which the needle is embedded can also adversely affect these drugs. As a partial solution to these problems, some pre-filled syringes are starting to be fabricated from certain inert plastics, which exhibit low protein absorption and high compatibility with biological drugs. To date, however, there is no such appropriate solution for long term drug containers for application in a patch-pump or patch-injector housing.

Patch-pumps or patch-injectors or micro-infusers, or other such devices that transfer drug from an external source onto or through the skin, are drug-delivery devices which ideally have a very slim profile and are relatively flat, so as to provide maximum comfort to the patient. Syringe-type drug reservoirs represent a very inefficient design of a drug reservoir in terms of minimizing the size of the patch-pump device. This is due to the fact that (a) the rigid cylindrical design of syringes require that the reservoir portion of the patch pump needs to have at least the thickness dictated by the diameter of the syringe plus the thickness of the walls of the housing, and (b) the initial length of the syringe reservoir needs to be at least the length of the portion of the syringe which holds the drug, plus the protruding length of the plunger.

One approach to integrating a relatively flat drug reservoir into a patch-pump is described in U.S. Pat. No. 7,250,037 in which the drug reservoir has a domed shape. This dome is bounded on one side by a multi-layer film and from the other by a "dished-out" section of a rigid plastic. A spring presses against the multi-layer film in order to dispense the drug. As this spring extends, said multi-layer film is pressed into the "dished-out" section in the rigid plastic, thereby expelling the drug. While this configuration does enable the actuator (in this case a spring) to expel the contents of the reservoir, in terms of space-efficiency it is non-optimal. The optimal exploitation of the volume would of course be the use of 100% of the volume of a cylinder defined by the depth of the reservoir (h) multiplied by its area ($\pi r^2$). For example, assuming that the dome is semi-spherical, with a radius of 15 mm, then the volume enclosed using this approach would be $\frac{2}{3}\pi r^3$ which is 9.3 mL; whereas the volume of a cylinder with this radius and equivalent depth (15 mm) would be 14.6 mL. Thus it is clearly more space-efficient to have a drug-reservoir design which more closely approximates a cylinder.

SUMMARY OF THE INVENTION

The present invention therefore describes an improved slim-profile patch-pump or patch-injector or micro-infuser drug-delivery system, based on the use of a substantially cylindrical drug-reservoir assembly, said reservoir being compressed by the displacement caused by an actuator—either directly or via a piston arrangement. Thus the drug reservoir of the present invention enables a more efficient use of space within a patch-pump, enabling the patch-pump to be smaller for a given volume of drug delivered than it would have been had a syringe-type or dome-shaped reservoir been employed. The drug reservoir of the present invention comprises walls where at least one of said walls is at least partially flexible; such that the drug dispenser can be compressed by pressing its walls together as the drug is being delivered to the patient. Furthermore, said walls are comprised of biocompatible plastic materials, inter alia, from cyclic olefin polymer (COP), or a cyclic olefin copolymer (COC), such that the reservoir is flat and compressible, yet break resistant and suitable for long-term storage of drugs, including biologics.

In one embodiment, this invention therefore provides a drug-delivery device comprising a substantially cylindrical drug-reservoir assembly having an upper and a base surface, and an actuator, both located within a rigid housing, and a drug administration unit, where said drug-reservoir assembly comprises at least one flexible wall and a constraining ring, such that the displacement generated by said actuator collapses said flexible wall towards the base of said drug-reservoir within the constraint of said restraining ring, thereby expelling the drug contents of said drug-reservoir towards said drug administration means.

The term "substantially cylindrical" when in regard to the drug-reservoir assemblies of this invention refers to an overall structure, having a substantially elliptical or circular cross section or profile. The term "substantially cylindrical" is to be understood to refer to a structure, which has an overall profile which is entirely cylindrical (i.e. appearing as a circular or elliptical profile), or one which essentially approximates such a shape, but may have certain imperfections, so that the profile is not perfectly circular or elliptical.

The drug-delivery devices of this invention will have an actuator, as described and embodied herein, which is located within a rigid housing, and located proximally to the drug-reservoir assembly, which is also located within the rigid housing. The arrangement of the displacement-generating actuator and drug-reservoir assembly is such that displacement generated by the actuator collapses at least a part of the wall of the drug-reservoir assembly, resulting in expulsion of the drug contained therein.

The drug dispensers of this invention can incorporate any desired drug or agent, or combinations of drugs or agents, for delivery via a suitable drug delivery device, as desired.

The drug dispensers of this invention will comprise both a drug reservoir and drug administration unit such as a needle, cannula or microneedle-array.

In one aspect, and representing an embodiment of this invention, the drug reservoir will be semi-flexible. According to this aspect, and in one embodiment, the drug reservoir is collapsible and consists of an upper wall, a base wall and a joint region between said upper wall and said base well; wherein at least one of the upper wall or base wall is substantially rigid and at least one of the upper wall, base wall, or joint region is substantially flexible. In one aspect, and representing an embodiment of this invention, each of the upper walls, base walls, and joint regions is substantially flexible. The term "semi-flexible" refers to the fact that each of the upper wall, base wall and joint regions are not all flexible, but rather at least one of the same is rigid. The invention also provides for a flexible drug reservoir, which term "flexible" according to this aspect, refers to the fact that each of the upper wall, base wall and joint regions are all flexible.

In some embodiments, the drug reservoir has an interior or comprises an interior-facing layer of the upper wall, base wall, joint region or combination thereof, which is comprised of a biocompatible polymer, such as a plastic, having the unique characteristics of promoting minimal degradation of the drug contained therein, minimal adsorption of the drug onto the interior surfaces of such a reservoir, or a combination thereof. Such plastics to date are known to comprise, inter alia, COP and COC, and will include others that satisfy these criteria, as will be appreciated by the skilled artisan.

In some embodiments, an interior or at least a first internal layer of the upper wall and base wall is substantially comprised of a cyclic olefin polymer, or a cyclic olefin copolymer.

In some embodiments, the drug reservoir of this invention has a volume capacity of from about 1 to about 20 ml and in some embodiments, the drug reservoir has a volume capacity of from about 3 to about 10 ml.

In some embodiments, the drug reservoir has a diameter of from about 20 to about 70 mm and in some embodiments, the drug reservoir has a height of about 1-5 mm.

In some embodiments, the drug-reservoir, is comprised of a multi-layer film, which comprises in at least one or some of its interior-facing surfaces/layers a biocompatible plastic such as COP or COC.

In some embodiments, the drug reservoir may be further comprised of additional layers which serve as a water vapor barrier, an oxygen or other gas barrier or a combination thereof.

In some embodiments, the drug reservoir may comprise further additional separation or tie-layers.

In some embodiments, the diameter or dimensions of the drug reservoir may be optimized to provide a desired rate or delivery dose of the drug or agent contained therewithin, or in some embodiments, the drug delivery device may include an internal or external controller, said controller allowing for control of the delivery of the contained drug or agent over time, and such controlled delivery is a contemplated aspect of this invention.

In some embodiments, the modular drug dispenser further comprises a drug administration unit which in turn comprises a conduit and an outlet.

In some embodiments, the conduit provides a passageway for a drug or agent contained within the drug reservoir to the drug administration unit, and in some embodiments, such conduit also serves as a passageway for the egress of such drug or agent through the outlet of the drug delivery unit. According to this aspect, and in some embodiments, the conduit is therefore in fluid communication with and operationally connected to both the drug reservoir and the outlet of the drug dispenser of this invention. In some embodiments, the conduit may be operationally connected to another channel or multiple channels, and in fluid communication therewith, such that the drug or agent contained within the drug reservoir may access the additional channel or channels and eventually egress via the outlet of the drug delivery device.

In some embodiments, the invention provides a patch-pump or patch-injector comprising the drug reservoir of this invention, as herein described, and an expanding or displacement-generating actuator operationally connected thereto, whereby upon expansion of said expanding actuator (or due to the displacement produced by said displacement-generating actuator), a loaded drug or agent contained there-within is expelled from the modular drug dispenser. According to this aspect, and in one embodiment, the actuator may comprise any expanding or expansion-creating material, an expanding or displacement-generating battery, a spring-driven displacement mechanism, a compressed-gas driven displacement mechanism, a displacement mechanism driven by the gas created as result of a chemical or other reaction, a clockwork-driven displacement mechanism or an expanding cell, or like device, as will be appreciated by the skilled artisan. In some embodiments, the expanding cell may include an electrochemical cell.

In some embodiments of a the patch-pumps and patch-injectors of this invention, upon engaging of the expanding or displacement-generating actuator, whereby lateral sections of the upper and/or base wall, which are flexible, may be incorporated within the housing, the joint region may be a section of the flexible wall, which is thus incorporated within the housing, as described.

In some embodiments, the patch-pump of this invention may further comprise a drug-administration unit comprising a micro-needle, micro-needle array, rigid cannula or soft cannula. In some embodiments, according to this aspect, such drug-administration unit will be operationally connected to an outlet of the drug-reservoir or reservoirs of this invention, such that egress of the drug and contact with or administration to a subject is effected thereby.

In some embodiments, the patch-pump of this invention will comprise two or more drug-reservoirs.

In some embodiments, the patch-pumps of this invention may be used in a method of drug delivery to a subject, whereby the drug or agent contained therewithin is brought into contact with a subject, via effecting egress therewith from a drug reservoir of the drug-delivery device of this invention.

BRIEF DESCRIPTION OF THE FIGURES

FIGS. 3A1, 3A2, 3B1, 3B2 and 3C1 and 3C2 are isometric cross-sectional views which illustrate successive stages of the depletion of said reservoir as it is compressed;

FIGS. 4A, 4B and 4C provide cross-sectional isometric views of said reservoir integrated into a patch-pump device in an initial state and a final state respectively;

FIG. 5 shows an isometric view of a further preferred embodiment of the drug reservoir of the present invention, where both walls are flexible; and FIGS. 6A, and 6B shows a still further embodiment of the drug reservoir, where the upper wall of the reservoir has a flexible section.

DETAILED DESCRIPTION OF THE FIGURES

Figure 1:
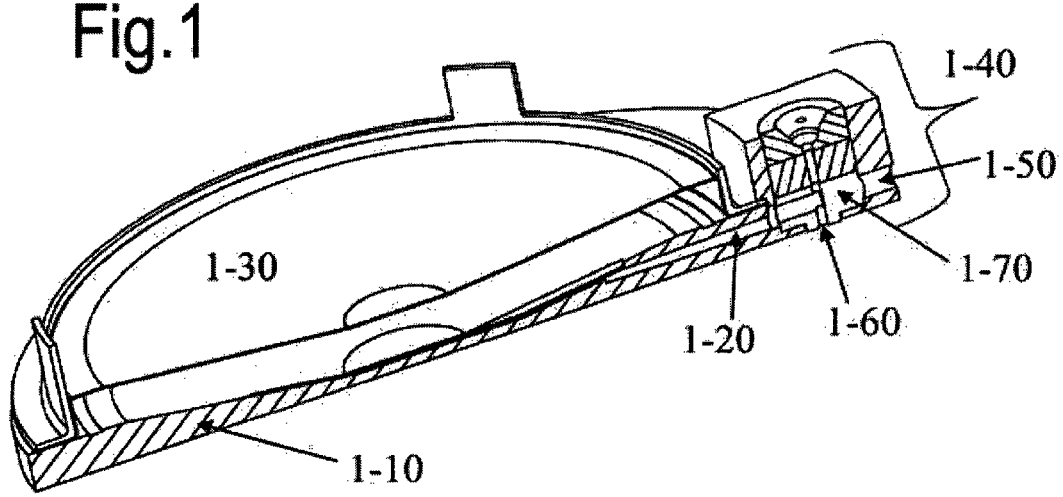
FIG. 1 shows an isometric cross-sectional view of a preferred embodiment of the drug reservoir assembly part of the present invention, in which one wall of the reservoir is rigid and one wall is flexible.

FIG. 1 shows an isometric exploded view of an embodiment of the drug-reservoir assembly of the present invention. This embodiment comprises a rigid base 1-10 including a drug conduit 1-20, a flexible upper wall 1-30 and a fitment or drug-administration unit, 1-40 in fluid connection with said conduit. The fitment may further comprise a filling (or inlet) channel 1-50 and an outlet 1-60 to a drug administration means such as a needle or cannula. The drug inlet/outlet channels may be sealed by a septum, a stopper or an external cap 1-70 until use. In order to ensure that the drug filled within the reservoir is only in contact with suitable materials; both the rigid base and the flexible upper wall comprise a biocompatible plastic, such as either COP or COC. For example, the rigid base will comprise, in some embodiments, a molded part formed of either a COP resin such as a Zeonor 1020R or Zeonex 690R/790R (from ZEON Corporation, Tokyo, Japan), or a COC resin such as TOPAS 6013S-04 (from TOPAS Advanced Polymers GmbH, Frankfurt-Höchst, Germany). The flexible upper wall comprises a multi-layer plastic film where the inner layer of said film (i.e. the one in direct contact with the drug) is also either a COP or a COC one. Such multi-layer films also include further layers, such as PCTFE (for water vapor barrier), EVOH (for oxygen barrier), together with tie-layers between the different layers. Suppliers for such flexible films include TekniPlex Europe N.V., Erembodegem, Belgium. Such multi-layer films use different layers to provide the various properties required—strength, barrier, etc.—together with a "contact layer" which is approved and/or biocompatible with the drug contained. In some cases this contact layer is PE; however, in the reservoir of the current invention, the contact layer of the flexible upper wall component is either COP or COC. Advantageously, this ensures that the drug in the reservoir is contacted-only by a suitable COP/COC layer, both as regards the rigid base and as regards the flexible upper wall.

Due to the employment of a substantially cylindrical design, the volume/space characteristics achieved by such a reservoir structure are highly optimal for a patch-pump or patch-injector, where achieving slim-profile for the overall pump is of paramount importance. For example, if a 3 mL reservoir is required, then it is sufficient to provide a reservoir of just 36 mm in diameter and with a collapsible inner height of 3 mm. As the drug volumes to be stored become greater, then the inherently advantageous nature of this design becomes even more apparent, as the volume capacity increases according to the square of the radius of the reservoir. Thus to store 6 mL (i.e. double the volume), it is merely required to increase the diameter to 51 mm, while keeping the other parameters constant. Also shown in this view is the conduit leading from near the center of the rigid base to the fitment on the external face of the patch-pump. This conduit may serve for filling the drug (at which point the flexible upper wall is raised to its upper position) and then as the outlet channel for the drug to the cannula or needle as the drug is delivered by the patch-pump to the patient. Advantageously, this conduit, together with the conical design of the rigid base, ensures minimum wastage of the drug as it is delivered, as described in more detail below.

Figure 2:
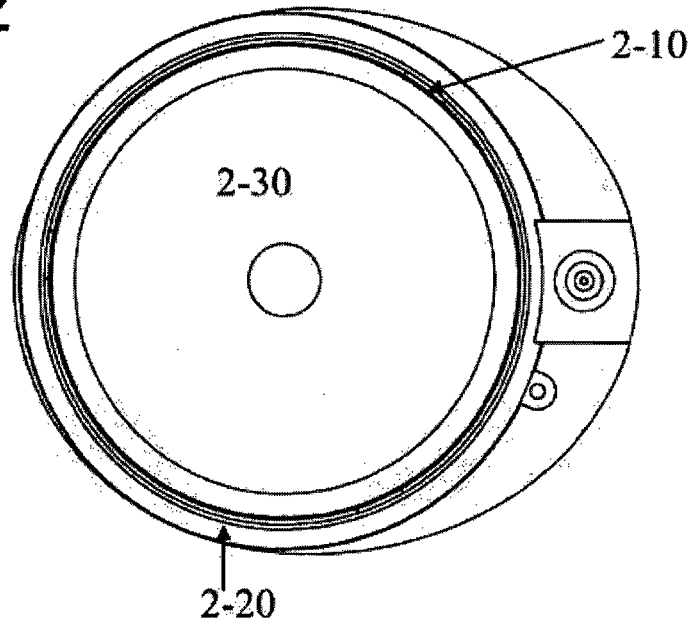
FIG. 2 shows a planar a view of the drug reservoir of FIG. 1.
Figure 7A:
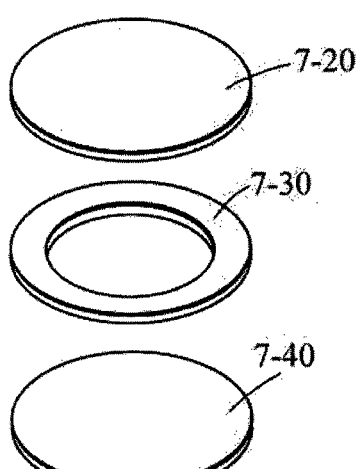
FIG. 7A-7D depicts a further embodiment of an actuator and its incorporation within a drug delivery device of the present invention.
Figure 7B:
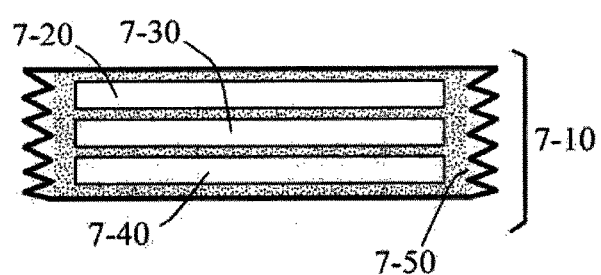
Figure 7C:
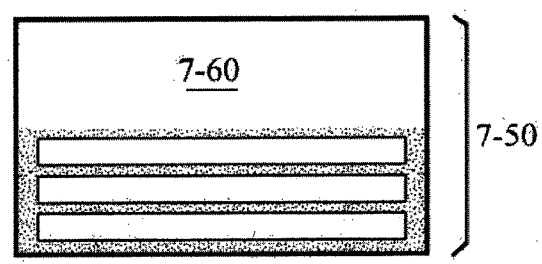
Figure 7D:
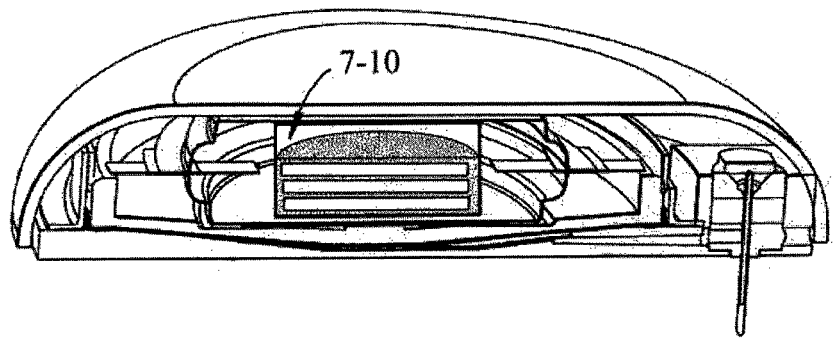

Referring now to FIG. 2, a planar view of the embodiment of the drug-reservoir of FIG. 1 is shown from above, showing a welding contour line 2-10 whereby the rigid base 2-20 and the flexible upper wall 2-30 are welded together. Said welding may be achieved by ultrasonic welding, where it is known in the art how to ultrasonically weld COP to COP or COC to COC, for example using ultrasonic welding equipment from Herrmann Ultrasonics Inc., Bartlett, Ill., USA or Rinco Ultrasonic AG Romanshorn, Switzerland. It may also be achieved by heat welding or laser welding, for example using laser welding equipment from Leister Process Technologies, Kaegiswil, Switzerland. Advantageously, such welding forms a strong seal between the rigid and flexible components of the reservoir. Another alternative is mechanical contact sealing, using a ring (not shown) to tightly hold the flexible component to the rigid one around the line shown as the welding line.

FIGS. 3A, 3B and 3C illustrate the operation of the drug-reservoir assembly as the drug-reservoir is compressed. To that end, also shown are a boundary wall 3-10 serving as a constraining ring which limits the sideways movement of the flexible wall 3-20 and enables proper folding or rolling of the flexible wall, and a piston 3-30 which serves to determine the upper contour of said flexible wall. Piston 3-30 is shown with outer piston wall 3-35. FIG. 3A shows the drug dispenser in its full state, with the full volume of drug contained within. FIG. 3A1 provides an exploded view of the circled region in FIG. 3A2, for ease of identification of the individual components referred to hereinabove. FIG. 3B shows the drug-reservoir state when half of the drug remains. Note that in this embodiment, the side portions 3-50 of the flexible wall 3-20 serve as a joint region connecting the upper flexible wall and the lower rigid wall. Said side portions fold or roll against themselves to form a concentric area as the reservoir is collapsed. FIG. 3B1 provides an exploded view of the circled region in FIG. 3B2, for ease of identification of the individual components referred to hereinabove. Referring now to FIG. 3C, the drug-reservoir assembly is here shown in its final empty state. In this state, and in the embodiment shown, the apex of the conical base of the piston 3-30 causes it to be guided towards the apex of the conical shape of the rigid base, thus ensuring that a maximum amount of the drug is forced out and therefore minimum wastage of drug occurs. FIG. 3C1 provides an exploded view of the circled region in FIG. 3C2, for ease of identification of the individual components referred to hereinabove.

As stated, due to its substantially cylindrical design, the drug-reservoir of the present invention is especially optimized for the requirements of a slim-profile patch-pump or patch-injector with high efficiency in terms of drug volume usage. FIG. 4A therefore provides an isometric exploded view of such a patch-pump in order to show the location and integration of the drug-reservoir therein. Note that in addition to the drug-reservoir 4-10, also shown are an actuator 4-20 for pressing against the piston and a needle 4-30 in fluid connection with the conduit 4-40 from said drug-reservoir; all within a housing 4-50. In the case that a control module is required to control the actuator, then such a control module will also be present within said housing. In the embodiment shown, the rigid base of the drug reservoir 4-60 also serves as the base of the pump housing, such that the need for an additional component is eliminated and the resulting patch-pump is slimmer in profile. The actuator 4-20 operates according to an expanding or displacement-generating principle, such that as it expands or otherwise generates a displacement, it presses against the drug dispenser 4-10, causing the drug to be delivered to the patient via a drug-administration means such as the needle 4-30 shown. FIG. 4A shows said actuator in its initial state, at which point the drug reservoir is full.

Referring now to FIG. 4C, the state at in which the actuator has expanded to its final dimensions is shown, by which point the reservoir has collapsed to its final (empty) state; meaning that the drug has been expelled via the conduit to the administration means (such as a needle). FIG. 4B shows an exploded view of the area marked in FIG. 4C.

As will be obvious to one skilled in the art, the patch-pump thus constructed may have a number of different embodiments, including but not limited to: (a) having a drug-administration unit chosen from the group including micro-needles, micro-needle arrays, flexible cannulas, needle-free and transdermal means; having an actuator which is an expanding battery which expands and/or causes a displacement as it is completed (as per WO2007010522, WO2007129317A1 or U.S. 61/310,135 and their subsequent national filings); (c) having an expanding or displacement-generating actuator operating according to a different principle, including but not limited to, spring or clockwork driven mechanisms, gas generation by electrolysis, and use of other expanding materials; (d) having more than one drug-reservoir assembly such that multiple drugs can be delivered; and (e) having an external controller for remote programming and/or control of the patch-pump. A further embodiment of an expanding or displacement-generating battery—more suitable for fast delivery over minutes or hours than those listed above—can be implemented using a battery chemistry in which a gas is developed internally within the sealed battery housing as a function of the discharge performed. In a preferred embodiment of such a battery, the reaction ($Zn+H_2O \rightarrow ZnO+H_2$) is self powered and uses a zinc electrode (negative) and an inert electrode for hydrogen evolution (positive) in an alkaline electrolyte such as one including NaOH. In one embodiment, the inert electrode is a platinized titanium mesh and the two electrodes are held apart by a non-conductive spacer. This reaction has a potential of 400 mV and occurs spontaneously when the electrodes are shorted or connected by a resistor. It is fully controllable and there is no gas generated when the connection is broken.

According to this aspect, and in one embodiment, such a gas-evolving battery may have an anode that comprises zinc (or, in other embodiments, cadmium or iron) and a cathode that is a hydrogen-evolving one, preferably made of high-surface-area metal material in grid, mesh, foam, sintered, fiber or mat form where the metal is preferably Ni, Co, Mo, Ti, Fe, steel, stainless steel and their alloys. In one embodiment said cathode material may be coated by a metal from the noble metals group (Pt, Pd, Au, Ir, Rh, Ru etc.) and/or other transition metals or alloys (for example, comprising Ni, Co, Mo, Ti, Fe, Mn, Hf etc.) as standalone coatings, or supported on an alkali stable carrier such as carbon or graphite. In a further embodiment, the cathode can be an intermetallic compound such as carbide, nitride, boride or a sulfide of metals, or a hydride precursor in the form AB5 or AB2. In compounds of the form AB5, A is a rare earth metal mixture of lanthanum, cerium, neodymium, neodymium and praseodymium (mischmetal) usually with vanadium, titanium and zirconium, and B is nickel, cobalt, manganese, vanadium and/or aluminum. In compounds of the form AB2, A is titanium and/or vanadium and B is zirconium or nickel, modified with chromium, cobalt, iron, and/or manganese.

In some embodiments, according to this aspect, incorporation of such a gas-generating battery may provide an advantage relative to other displacement-generating batteries, in terms of speed of performance and thereby the ability to as it works faster and can deliver the entire contents of the drug reservoir in minutes rather than hours.

Also included within the scope and claims of the present invention are a number of other preferred embodiments of the drug reservoir, providing only that at least one of the reservoir's walls has an at least partially flexible wall such that the compression of such reservoir by the actuator as illustrated in FIGS. 4aA and 4B causes the drug in said reservoir to be expelled. For example, FIG. 5 shows a further preferred embodiment of the drug reservoir of the present invention, where both upper wall 5-10 and base wall 5-20 are flexible and connected via the joint region 5-30. In this embodiment, the dispenser has a bladder-type structure, where both walls are comprised of the multi-layer film having the contact layer made from COP or COC, and these two sides are preferably welded together. In this structure, the join region 5-30 may serve as the constraining ring maintaining the substantially cylindrical structure, or alternatively, an external rigid ring (not shown but similar to above) may serve this purpose.

A further such embodiment is shown in FIG. 6, comprising a rigid base 6-10 and a mostly rigid upper wall 6-20 (potentially also functioning as a piston). In said embodiment said mostly rigid upper wall 6-20 of the reservoir has a flexible section 6-30 around its circumference. In this embodiment, said flexible section 6-30 is the joint region which serves as the part which is "rolled" as per the explanation in FIGS. 3A to 3C, enabling the reservoir to be compressed. In one embodiment, said flexible section is co-molded with the rest of the upper wall, such that the inner layer of this entire partially flexible upper wall of the reservoir is made of either COP or COC. FIG. 6B shows an exploded view of FIG. 6B, which provides for ease of view of the indicated components referred to hereinabove. A rigid constraining ring is provided as per the embodiment shown in FIGS. 1-3.

FIG. 7 presents another embodied drug delivery device, in which insertion of one embodied gas evolving 7-10 actuator is shown. In FIG. 7A an exploded isometric view of a gas-evolving battery arrangement is shown, where an anode 7-20 (in some embodiments, zinc-based) and cathode 7-40 are shown (in some embodiments, a mesh or foam based cathode) are separated by a separator 7-30 (in some embodiments, made of plastic), which anode and cathode are further provided with appropriate connectors to a control circuit, in order to discharge the battery. FIG. 7B demonstrates an embodied housing and arrangement of the battery of FIG. 7A, wherein the anode 7-20, cathode 7-40 and separator 7-30 are shown together with the electrolyte. The housing may contain lateral modifications 7-50, such that expansion of the housing to accommodate the evolved gas, 7-60 may occur. FIG. 7D depicts an embodied insertion of the gas-evolving actuator within an embodied drug-delivery device in the expanded state.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or sub-range within the stated ranges, optionally including or excluding either or both endpoints, in different embodiments of the invention, to the tenth of the unit of the lower limit of the range, unless the context clearly dictates otherwise.

It will be apparent to those skilled in the art that various modifications and variations can be made in the drug-reservoirs, patch-pumps, kits and methods of the present invention without departing from the spirit or scope of the invention.

In some embodiments, the term "comprise" or grammatical forms thereof, refers to the inclusion of the indicated components of this invention, as well as inclusion of other components, as are known in the drug delivery device industry.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In one embodiment of this invention, "about" refers to a quality wherein the means to satisfy a specific need is met, e.g., the values regarding height, diameter, etc., may be largely but not wholly that which is specified but it meets the specific need of a slim profile dispenser which delivers a desired quantity of a drug or agent. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2. In some embodiments, the term "about" with regard to a reference value encompasses a deviation from the amount by no more than 5%, no more than 10% or no more than 20% either above or below the indicated value.

In the claims articles such as "a", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A drug delivery device comprising a substantially cylindrical drug-reservoir assembly, said substantially cylindrical drug-reservoir assembly comprising:
   a collapsible semi-flexible drug reservoir chamber, the chamber having an interior defined by a flexible upper wall, a rigid base wall and a joint region between said flexible upper wall and said rigid base wall;
   a housing;
   a rigid constraining ring, which constraining ring substantially surrounds outer boundaries of the flexible upper wall, the rigid base wall or a combination thereof of said collapsible semi-flexible drug reservoir chamber, and wherein:
      the constraining ring is disposed within the housing,
      the constraining ring is separate from the housing, and
      the constraining ring is separate from the rigid base wall;
   a drug administration unit in fluid communication with said semi-flexible drug reservoir chamber; and
   a displacement-generating actuator, located proximally to said semi-flexible drug reservoir chamber, wherein the displacement-generating actuator moves perpendicular to a patient skin surface upon which the drug delivery device is placed;
   whereby displacement generated by said displacement-generating actuator operationally connected to said semi-flexible drug reservoir chamber, causes said flexible upper wall to collapse, promotes folding or rolling of said flexible upper wall between the displacement actuating generator and the constraining ring as said flexible upper wall collapses against the rigid base wall of said semi-flexible drug reservoir chamber within the constraints of said rigid constraining ring surrounding a circumference of said flexible upper wall, which further causes substantially expelling drug contents of said semi-flexible drug reservoir chamber toward said drug administration unit thereby delivering said drug contents from said drug delivery device.

2. The drug delivery device of claim 1, wherein said joint region is substantially flexible.

3. The drug delivery device of claim 1 where the upper wall comprises an interior-facing layer comprising a plastic selected from the group consisting of COP (cyclic olefin polymer) and COC (cyclic olefin copolymer), the base wall comprises an interior-facing layer comprising a plastic selected from the group consisting of COP (cyclic olefin polymer) and COC (cyclic olefin copolymer), and the joint region comprises an interior-facing layer comprising a plastic selected from the group consisting of COP (cyclic olefin polymer) and COC (cyclic olefin copolymer), for long-term storage of drugs.

4. The drug delivery device of claim 1 where said displacement-generating actuator comprises a member selected from the group consisting of a spring, a hydrogel or an expanding material selected from the group consisting of a compressed sponge, a gas-generating assembly, a clockwork mechanism and a displacement-generating battery.

5. The drug delivery device of claim 4 wherein said displacement-generating actuator comprises said displacement-generating battery, and where said battery comprises electrodes and electrolyte such that the discharge or charge of said battery causes the total volume of said electrode and electrolyte to expand, thereby generating said displacement.

6. The drug delivery device of claim 4 wherein said displacement-generating actuator comprises said displacement-generating battery, and where said displacement-generating battery generates gas internally as said battery is discharged or charged, causing the battery to expand and generate said displacement.

7. The drug delivery device of claim 1,
wherein said semi-flexible drug reservoir chamber has a volume capacity of from about 1 to about 20 ml,
wherein said semi-flexible drug reservoir chamber has a volume capacity of from about 3 to about 10 ml,
wherein said semi-flexible drug reservoir chamber has a diameter of from about 20 to about 70 mm, or
wherein said semi-flexible drug reservoir chamber has a height of from about 1 mm to about 5 mm.

8. The drug delivery device of claim 1, wherein said semi-flexible drug reservoir chamber comprises a multi-layer plastic film.

9. The drug delivery device of claim 8, wherein said multi-layer plastic film comprises additional layers which serve as a water vapor barrier, an oxygen barrier or a combination thereof, and wherein said multi-layer plastic film has further additional separation or tie-layers.

10. The drug delivery device of claim 1, wherein said semi-flexible drug reservoir chamber contains a drug therein.

11. The drug delivery device of claim 1, wherein said drug administration unit comprises a micro-needle, a micro-needle array, a rigid cannula or a soft cannula.

12. The drug delivery device of claim 1, further comprising one or more collapsible semi-flexible drug reservoir chambers.

13. A method of drug delivery to a subject comprising contacting a subject with the drug delivery device of claim 1.

14. The drug delivery device of claim 1, wherein said joint region is substantially flexible, and wherein said displacement generated by said displacement-generating actuator causes said substantially flexible joint region to collapse and promotes folding or rolling of said substantially flexible joint region as the substantially flexible joint region collapses.

15. The drug delivery device of claim 1, wherein a piston of the displacement-generating actuator moves relative to the constraining ring and the housing as a result of the displacement generated by the displacement-generating actuator.

16. The drug delivery device of claim 1, wherein the constraining ring limits sideways movement of the joint region while said drug contents are delivered from said drug delivery device.

17. The drug delivery device of claim 1, wherein the joint region folds against itself to form a concentric area as a result of the displacement generated by the displacement-generating actuator.

18. The drug delivery device of claim 1, wherein a piston of the displacement-generating actuator slides concentrically within the constraining ring as a result of the displacement generated by the displacement-generating actuator.

19. The drug delivery device of claim 1, wherein the constraining ring remains stationary relative to the housing while said drug contents are delivered from said drug delivery device.

20. The drug delivery device of claim 1, wherein the joint region folds against itself between the constraining ring and a piston of the displacement-generating actuator as a result of the displacement generated by the displacement-generating actuator.

21. The drug delivery device of claim 1, wherein the constraining ring and a piston of the displacement-generating actuator are disposed to provide a space therebetween that promotes folding of the joint region against itself as a result of the displacement generated by the displacement-generating actuator.

22. The drug delivery device of claim 1, wherein said displacement generated by said displacement-generating actuator promotes folding or rolling of said flexible upper wall between the rigid constraining ring and said displacement-generating actuator as the displacement-generating actuator moves perpendicular to the patient skin surface upon which the drug delivery device is placed.

23. The drug delivery device of claim 1, wherein said flexible upper wall and said rigid base wall of said collapsible semi-flexible drug reservoir chamber are welded together.

24. The drug delivery device of claim 23, wherein said flexible upper wall and said rigid base wall of said collapsible semi-flexible drug reservoir chamber are welded together via a circular welding contour line.

25. The drug delivery device of claim 1, wherein said displacement-generating actuator comprises an outer piston wall, wherein said constraining ring is disposed between said housing and said outer piston wall, and wherein said constraining ring is parallel with said outer piston wall.

26. The drug delivery device of claim 1, wherein said constraining ring is perpendicular to said rigid base wall at a point on said rigid base wall where said constraining ring contacts said rigid base wall.

* * * * *